(12) United States Patent
Fraga et al.

(10) Patent No.: US 10,387,107 B2
(45) Date of Patent: *Aug. 20, 2019

(54) UTILIZING ATHLETIC ACTIVITIES TO AUGMENT AUDIBLE COMPOSITIONS

(71) Applicant: NIKE, Inc., Beaverton, OR (US)

(72) Inventors: Justin Fraga, Portland, OR (US); Harold L. Lindstrom, Jr., Portland, OR (US); Willoughby H. Walling, Portland, OR (US); Christopher Andon, Portland, OR (US); Kristopher J. Schultz, Columbus, OH (US); Eric S. Mcgary, Columbus, OH (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/221,224

(22) Filed: Jul. 27, 2016

(65) Prior Publication Data
US 2017/0031650 A1   Feb. 2, 2017

Related U.S. Application Data

(60) Provisional application No. 62/199,655, filed on Jul. 31, 2015.

(51) Int. Cl.
*G06F 17/00* (2006.01)
*G06F 3/16* (2006.01)
(Continued)

(52) U.S. Cl.
CPC ............. *G06F 3/165* (2013.01); *A61B 5/024* (2013.01); *G06F 3/04842* (2013.01);
(Continued)

(58) Field of Classification Search
CPC ........... G10H 1/0025; G10H 2240/085; G10H 2250/311; H04S 3/008
See application file for complete search history.

(56) References Cited

U.S. PATENT DOCUMENTS

| 2009/0158920 A1* | 6/2009 | Itami | A63B 24/0062 84/645 |
| 2014/0052282 A1* | 2/2014 | Balassanian | G06F 17/30778 700/94 |
| 2014/0354434 A1* | 12/2014 | Lalonde | G06F 17/30017 340/573.1 |

FOREIGN PATENT DOCUMENTS

WO   2010041147 A2   4/2010

OTHER PUBLICATIONS

Oct. 24, 2016—(WO) ISR & WO—App. No. PCT/US16/044611.

* cited by examiner

*Primary Examiner* — Thomas H Maung
(74) *Attorney, Agent, or Firm* — Banner & Witcoff, Ltd.

(57) ABSTRACT

Example embodiments relate to methods and systems for playback of adaptive music corresponding to an athletic activity. A user input is received from a user selecting an existing song for audible playback to the user, the song comprising a plurality of audio layers including at least a first layer, a second layer, and a third layer. Augmented playback of the existing song to the user is initiated by audibly providing the first layer but not the second layer. Physical activity information derived from a sensor corresponding to a real-time physical activity level of a user is received. If the physical activity level of the user is above a first activity level threshold, the augmented playback of the existing song is continued by audibly providing the first layer and the second layer to the user.

20 Claims, 9 Drawing Sheets

(51) Int. Cl.
  *A61B 5/024*      (2006.01)
  *G10L 25/21*      (2013.01)
  *G06F 3/0484*     (2013.01)
  *G06F 19/00*      (2018.01)
  *G10H 1/00*       (2006.01)
  *H04S 3/00*       (2006.01)
(52) U.S. Cl.
  CPC .......... *G06F 19/3481* (2013.01); *G10L 25/21*
  (2013.01); *G10H 1/0025* (2013.01); *G10H*
  *2240/085* (2013.01); *G10H 2250/311*
  (2013.01); *H04S 3/008* (2013.01)

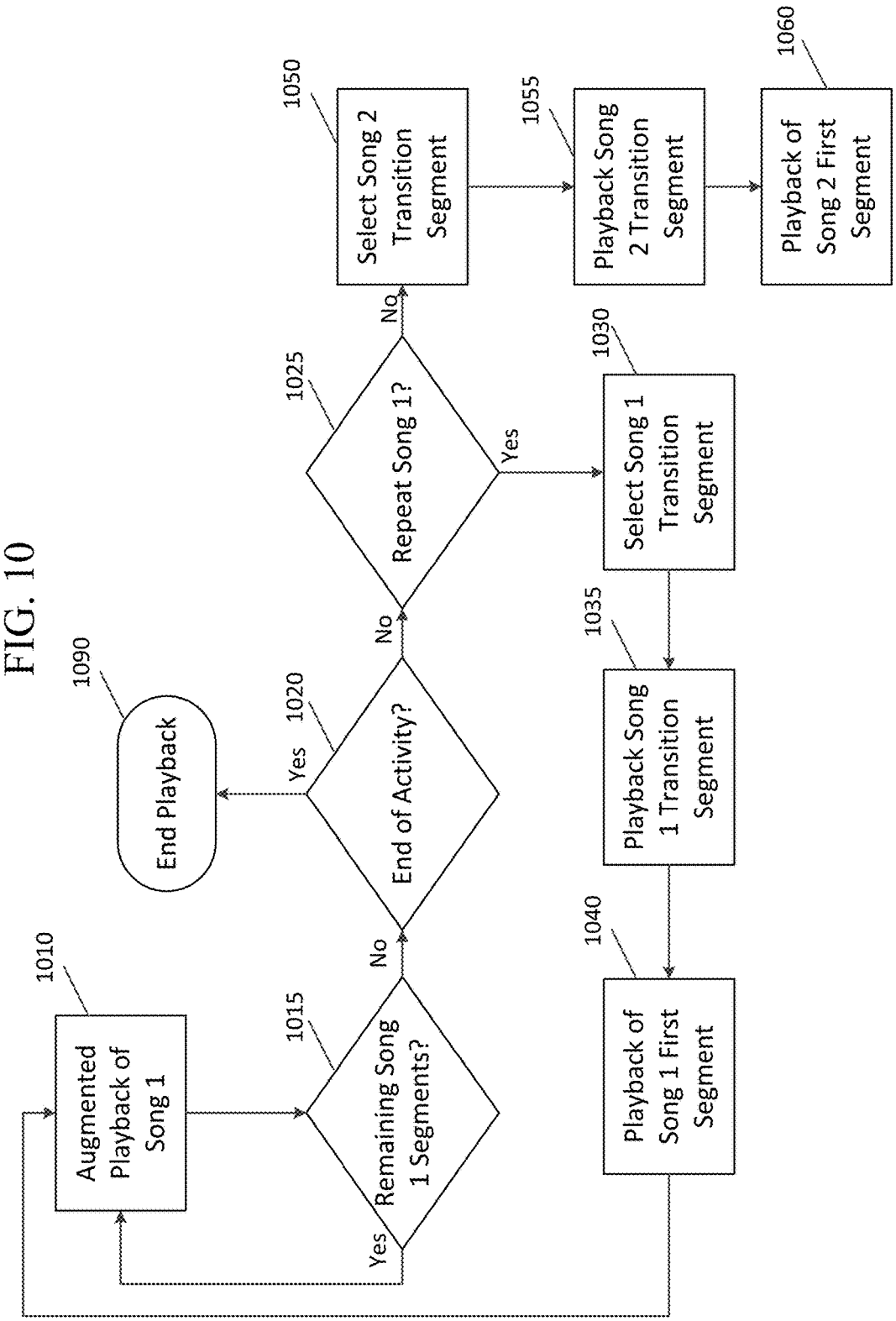

UTILIZING ATHLETIC ACTIVITIES TO AUGMENT AUDIBLE COMPOSITIONS

CROSS-REFERENCE TO RELATED APPLICATION

The present application claims priority to and is a non-provisional filing of U.S. Provisional Application Ser. No. 62/199,655, filed Jul. 31, 2015, and entitled "Utilizing Athletic Activities to Augment Audible Compositions," the entire contents of which are incorporated by reference herein in their entirety.

FIELD OF THE INVENTION

Aspects of this invention relate generally to systems and methods for generating an athletic training program and the selection of music in association therewith. In particular, aspects of this invention relate to playback of adaptive music corresponding to an athletic activity.

BACKGROUND

While most people appreciate the importance of physical fitness, many have difficulty determining an appropriate exercise program for reaching their desired goal. Further, some people find it difficult to maintain an exercise regimen without some entertainment such as music to keep them motivated through the exercise program.

Athletes have found that listening to music while running may improve endurance and enjoyment of the physical activity. In particular, some types of music may be more beneficial to increasing the athletic activity of an individual than others. For example, music with fast tempos may encourage an athlete to run faster and/or farther. Existing systems that alter tempo alone distract the user's enjoyment of the music. In certain instances, "coaching" athletes to work harder may discourage athletic activity. Systems that attempt to create entirely new music often don't take into account a user's likes and dislikes and/or accurately reflect their exertion level and/or a desired exertion level.

Therefore, improved systems and methods to address these and other shortcomings in the art are desired.

SUMMARY

The following presents a general summary of aspects of the invention in order to provide a basic understanding of at least some of its aspects. This summary is not an extensive overview of the invention. It is not intended to identify key or critical elements of the invention and/or to delineate the scope of the invention. The following summary merely presents some concepts of the invention in a general form as a prelude to the more detailed description provided below.

One or more aspects describe systems, apparatuses, computer readable media, and methods for selecting and playing streamed audio tracks during an athletic activity. A computing device may receiving a user input from a user selecting an existing song for audible playback to the user, the song comprising a plurality of audio layers including at least a first layer, a second layer, and a third layer, wherein the first layer includes audio information for a first musical instrument and the second layer includes audio information for a second musical instrument. Augmented playback of the existing song is initiated to the user by audibly providing the first layer but not the second layer. Physical activity information derived from a sensor corresponding to a real-time physical activity level of a user is received. Upon determining that the real-time physical activity level of the user is above a first activity level threshold, the augmented playback of the existing song is continued by audibly providing the first layer and the second layer to the user.

According to another aspect of the present disclosure, a computing device may electronically access an existing song for audible playback to the user, the song comprising a plurality of audio layers that are individually and selectively overlaid an entire duration of the existing song. The duration may include a plurality of sequential segments comprising at least a first segment and a last segment. The plurality of audio layers may include at least a first layer, a second layer, and a third layer, wherein the first layer includes audio information for a first musical instrument and the second layer includes audio information for a second musical instrument that is not within the first layer. Each of the plurality of segments may be associated with an exertion level based upon audible characteristics of the respective segments. Augmented playback of the first segment of the existing song may be initiated to the user by audibly providing the at least one layer of the plurality of layers, however, without at least one layer within the plurality of layers. Before initiating playback of the last segment, physical activity information derived from a sensor corresponding to a real-time physical activity level of the user may be received at a first instance. Based on the physical activity information received at the first instance, an exertion level of the user may be determined with respect to at least one physical activity parameter. Based on the determined exertion level, at least one of the plurality of segments may be selected as a candidate transition segment for transitioning the user to. Based on the selected candidate transition segment, a plurality of audible pathways may be identified to transition the user to the selected candidate transition segment without playing all of any sequential segments between a current location of the existing song and the transition locations. Each of the plurality of audible pathways and a first pathway from the plurality of audible pathways may be selected. The first pathway of the existing song may be audibly provided to arrive at the candidate transition segment, and providing a sequential segment of the plurality of segments may be audibly provided to the user following playback of the candidate transition segment.

In some embodiments, the present invention can be partially or wholly implemented on a computer-readable medium, for example, by storing computer-readable instructions or modules, or by utilizing computer-readable data structures.

Of course, the methods and systems of the above-referenced embodiments may also include other additional elements, steps, computer-executable instructions, or computer-readable data structures.

The details of these and other embodiments of the present invention are set forth in the accompanying drawings and the description below. Other features and advantages of the invention will be apparent from the description and drawings, and from the claims.

BRIEF DESCRIPTION OF THE DRAWINGS

A more complete understanding of the present invention and certain advantages thereof may be acquired by referring to the following description along with the accompanying drawings, in which like reference numbers indicate like features, and wherein:

FIG. 10 shows a flowchart of a method for subsequent song determination for augmented playback of adaptive music during a physical activity.

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
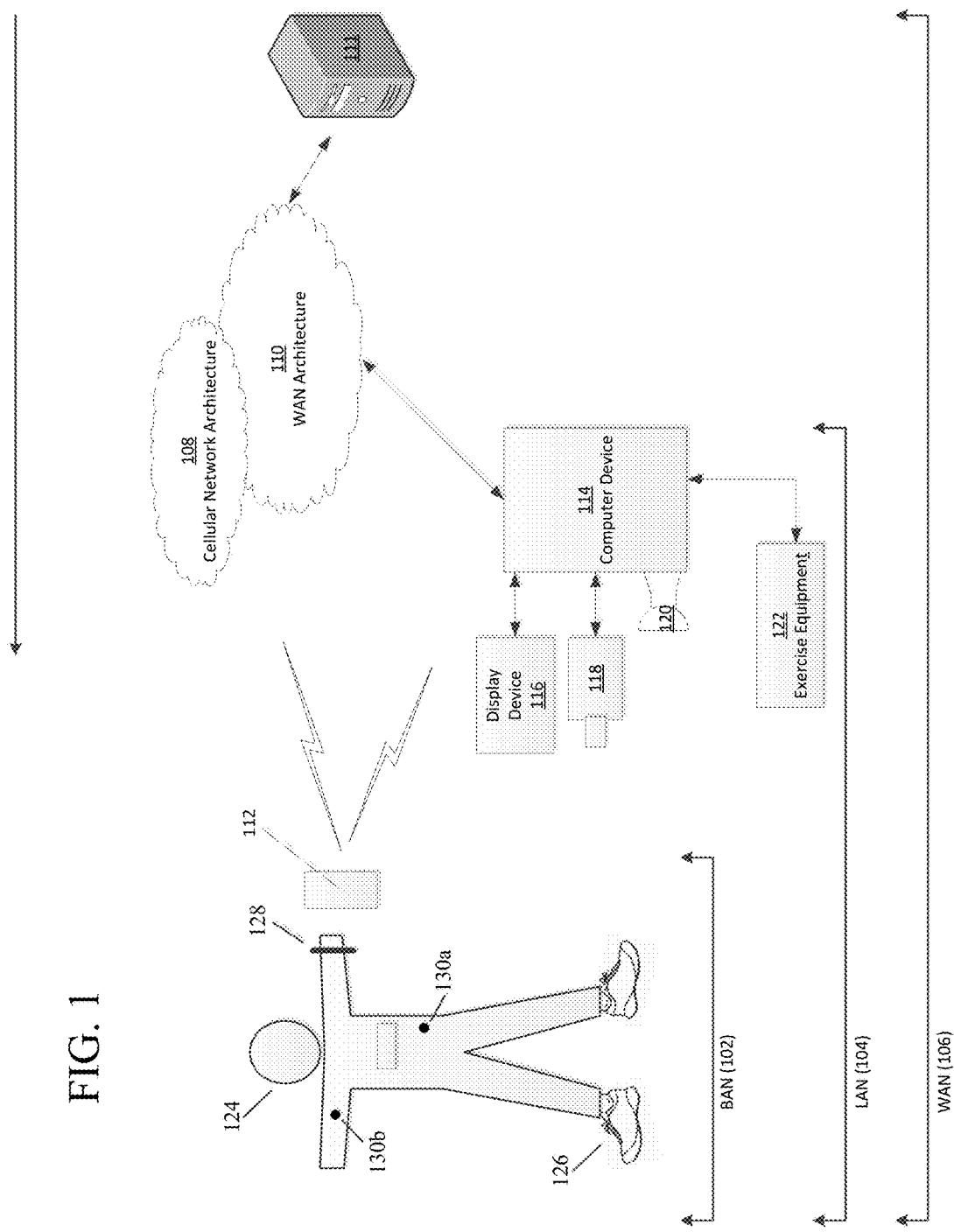
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
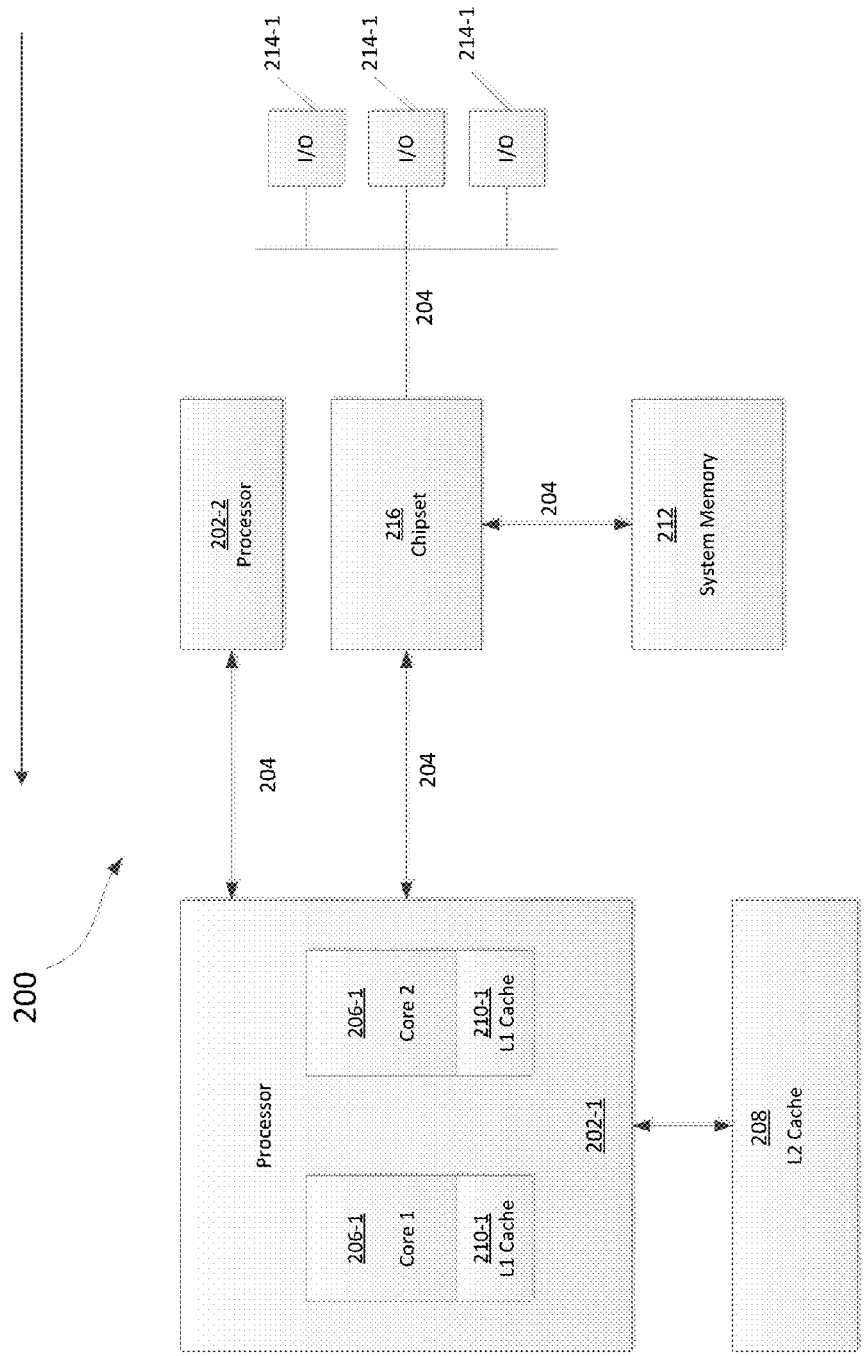
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, PAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
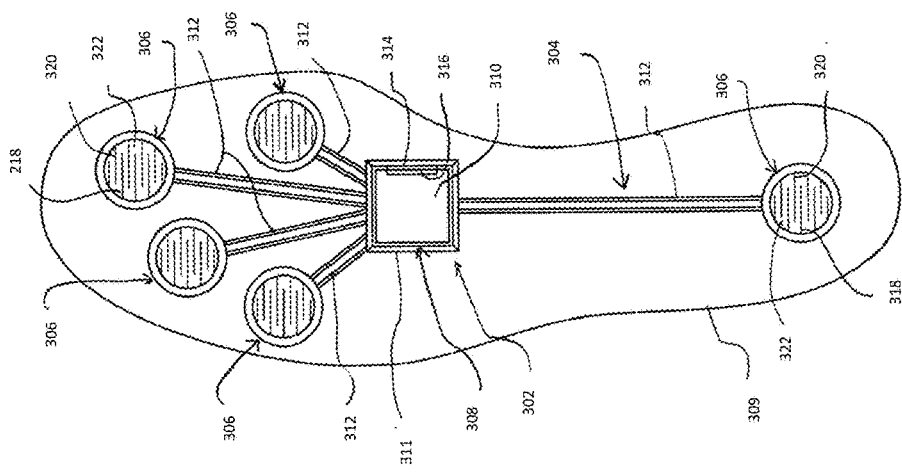
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
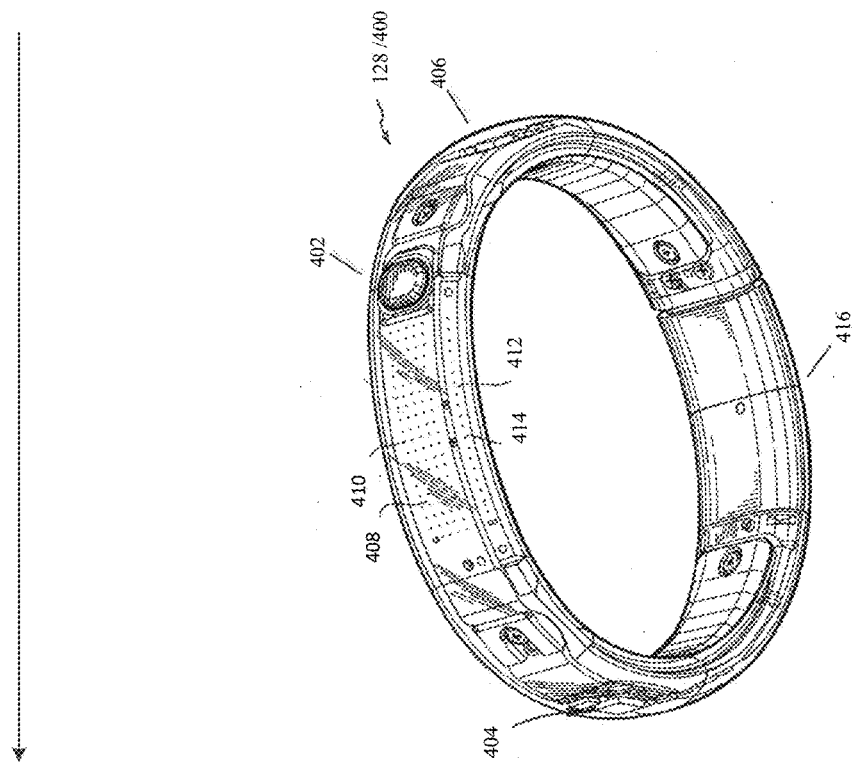
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
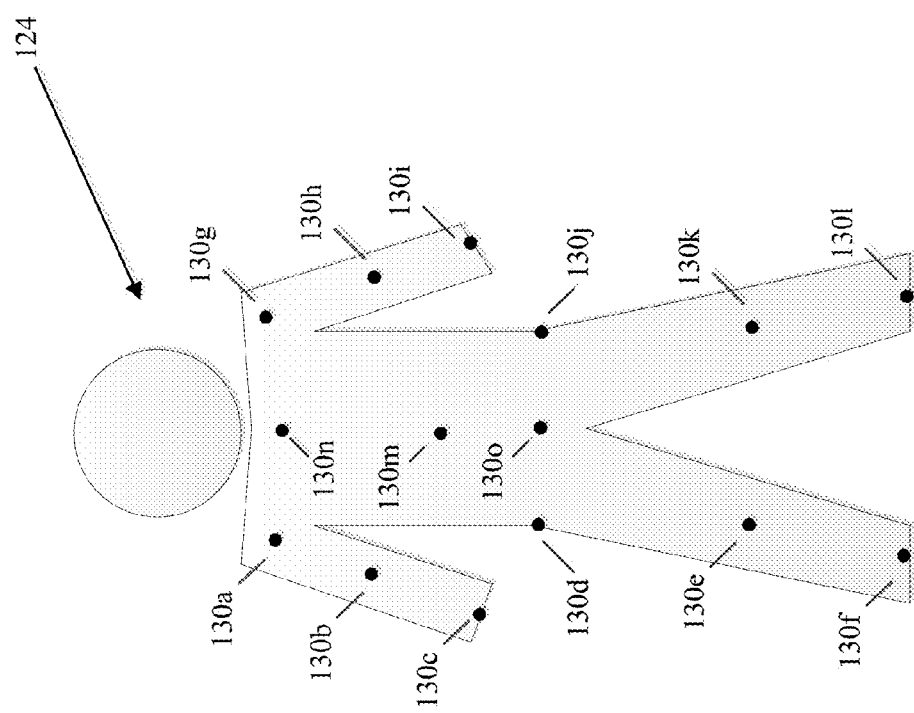
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 1306n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple sensor locations, such as sensors 130*m*-130*o*, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130*m*-130*o* may serve as a point for a center of moment location of user 124. In another embodiment, one or more locations may serve as a center of moment of specific body parts or regions.

II. Example Adaptive Music Playback Systems with Audible Layers

Figure 6:
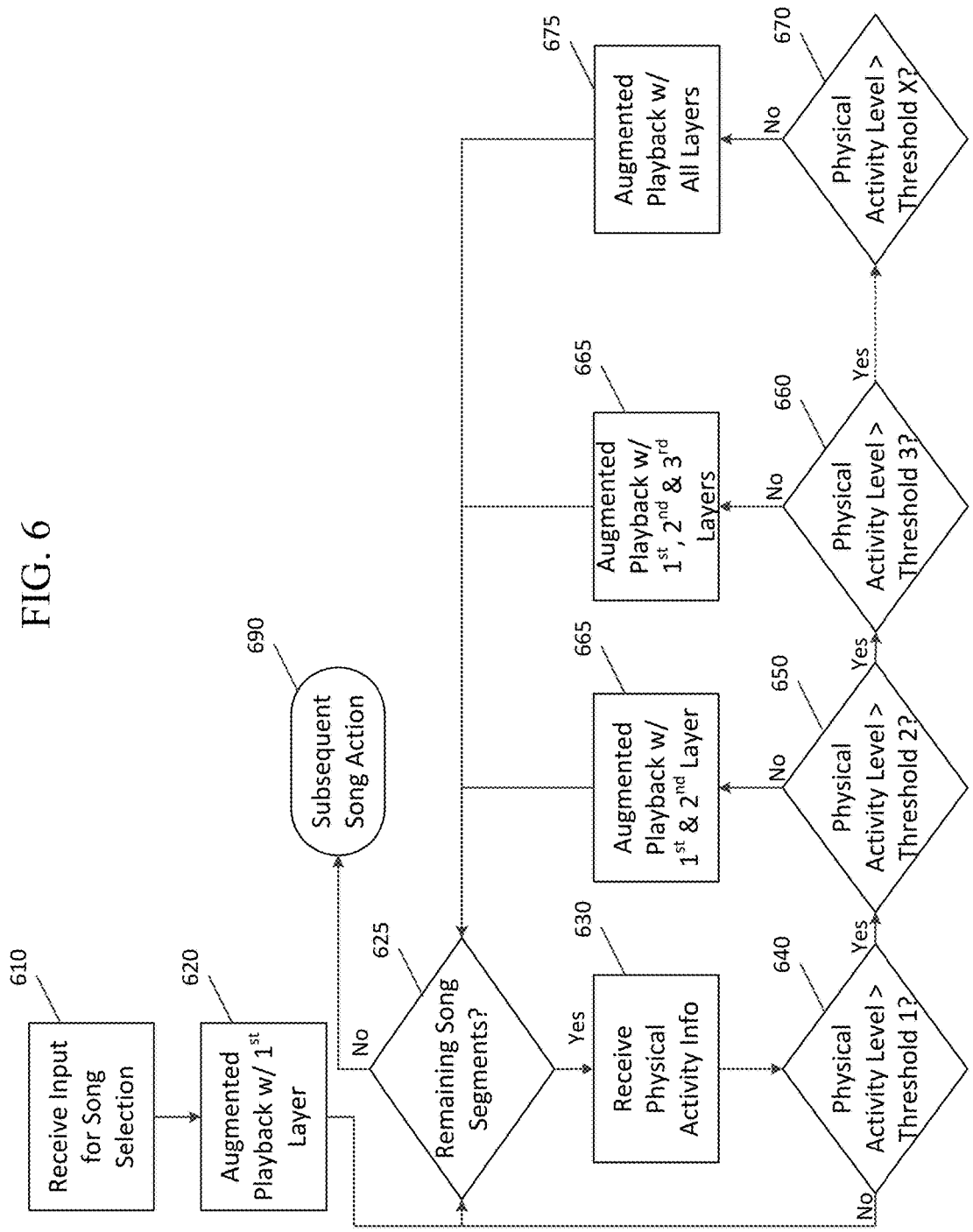
FIG. 6 shows a flowchart of a method for augmented playback of adaptive music during a physical activity.

FIG. 6 illustrates an embodiment of a process for augmenting the audible playback of an electronic file containing audible data, such as a musical composition. In this regard, the terms "musical composition", "song" and similar phrases are used throughout this disclosure to refer to specific illustrative examples, however, those skilled in the art will readily appreciate that any electronic collection of audible data is within the scope of this disclosure. In certain embodiments, one or more audible notes within a composition may be created from one or more instruments, including musical instruments (including a voice), digital manipulation devices and/or combinations thereof. In accordance with one embodiment, an existing collection, such as a known or existing song according to detected changes in a physical activity level of a user. In some embodiments, some of the following steps may be accomplished by various components, systems or devices associated with an adaptive music playback system. It will be understood that in other embodiments one or more of the following steps may be optional.

At 610, an existing song is electronically accessed for audible playback to the user, e.g., upon receiving a user input selecting the existing song. The song may be composed of a plurality of audio layers that are individually and selectively overlaid on an entire duration of the existing song. The duration may include a plurality of sequential segments including at least a first and a last segment. The first segment may correspond to a beginning of the song and the last segment may correspond to an end of the song. Further, the plurality of sequential segments may include any number of middle segments in addition to the first and last segments. For example, the existing song may be segmented into a plurality of segments. Segmenting the existing song may include receiving audible characteristic information of the song and dividing the song into the plurality of segments based on the audible characteristic information.

The plurality of audio layers may include first, second, and third layers. The plurality of audio layer may correspond to various musical instruments, for example, from a plurality of stem files associated with the song. In some examples, the first layer includes audio information for a first musical instrument, the second layer includes audio information for a second musical instrument that is not within the first layer, and the third layer includes audio information for a third musical instrument that is not within the first or second layers. In some examples, the first layer includes audio information for a first musical instrument, the second layer includes audio information for first and second musical instruments, and the third layer includes audio information for first, second and third musical instruments. The layers may correspond to various pluralities of musical instruments. In some examples, the first layer may comprise audio information for a first plurality of musical instruments and the second layer may comprise audio information for a second plurality of musical instruments. In some instances, musical instruments included in the first plurality of musical instruments may be excluded from the second plurality of musical instruments. In some examples, the third layer may include audio information configured to augment the audible perception of at least one of the first layer and the second layer when provided to the user. As referred to herein, musical instruments may include any number of various known instruments, voices and/or other sounds that can be stored as individual sound files. In some examples, one or more layers, e.g., higher layers, may include additional audio effects that are not included in the existing song. The layers may correspond to various stem files of the existing song. In some examples, the first layer may be composed of a first stem file and the second layer may be composed of a second stem file. Further the song may be composed of less than three layers or more than three layers without departing from the scope of these disclosures.

Each of the plurality of sequential segments may be associated with an exertion level, i.e., a physical activity level, based upon audible characteristics of the segments as described herein.

At 620, augmented playback of the first segment of the existing song is initiating to the user by audibly providing at least one layer of the song without at least one layer of the plurality of layers, e.g., the first layer of the song, but not the second layer of the song. In some examples, the plurality of layers of the existing song may be stored on a single non-transitory computer-readable medium prior to the user selecting the playback of the existing song, and the augmented playback of the existing song is from the single non-transitory computer-readable medium. Playback of the existing song may be initiated upon a user starting a physical activity, and the initial playback occurs during a warmup for the physical activity. During the warmup playback of song may be desirable at a lower energy level, e.g., a lower cadence and/or a lower volume intensity. Accordingly playback may be initiated with only a first layer to correspond to this lower energy level.

At 630, upon determining that there are remaining song segments of the song to be played at 625 (e.g., before initiating playback of the last segment of the song), physical activity derived from a sensor as described herein is received at a first instance, corresponding to a real-time physical activity level of a user. The physical activity information may include any parameter, such as from one or more sensors described herein. In certain embodiments, the physical activity information includes one of a pace of the user and/or a heart rate of the user. Based on the physical activity information received at the first instance, a real-time physical activity level of the user is obtained, e.g., an exertion level of the user with respect to at least one physical parameter is determined. The real-time physical activity level of the user may be compared to a first activity threshold to determine if the real-time activity level is above the first activity threshold at 640. In response to determining the physical activity level is above the first activity threshold, augmented playback of the existing song is continued by audibly providing the first layer and the second layer at 665. If the physical activity is determined to not be above the first activity threshold, playback with only the first layer may continue at 620. The second layer of the existing song may be received via a wireless transceiver. Further, after determining that the real-time physical activity level of the user is above the first activity level threshold, the real-time physical activity level may next be compared to a second activity level threshold to determine if the real-time activity is above a second activity level threshold 650. In response determining that the physical activity level is above the second activity threshold, augmented playback of the existing song by audibly providing the first layer, second layer, and third layer to the user at 665. This process may continue for any number of activity level thresholds up to a maximum activity level threshold X. If the physical activity level is determined to be above the activity level threshold X at 670, augmented playback with all layers of the song may be audibly provided to the user at 675.

Throughout the playback of the first song, the system will determine if there are a preset number of remaining song segments of the song to be play at 625. If there are remaining song segment, the physical activity information may be compared to the various activity thresholds and the playback of the song with a number of layer may be modified accordingly. Alternatively, if determined that there are not remaining song segments to be played at 625, a subsequent song action may occur at 690, e.g., ending the audible playback, repeating the song, selecting another song, and the like.

If the physical activity information does not exceed the first activity threshold, augmented playback of the existing song may continue, e.g., for a second segment of the song, a third segment of the song and so on, for a duration of the song while the physical activity information does not exceed the first activity threshold. In some examples, before initiating playback of the last segment or a predefined number of segments before the last song, playback of the existing song may be repeated, with the physical activity information remaining below the first activity threshold. In repeating playback of the existing song, at least one of the plurality of segments may be selected to as a loop transition segment for transitioning playback of the song back to the first segment.

III. Example Adaptive Music Playback Systems with Song Segments

Figure 7:
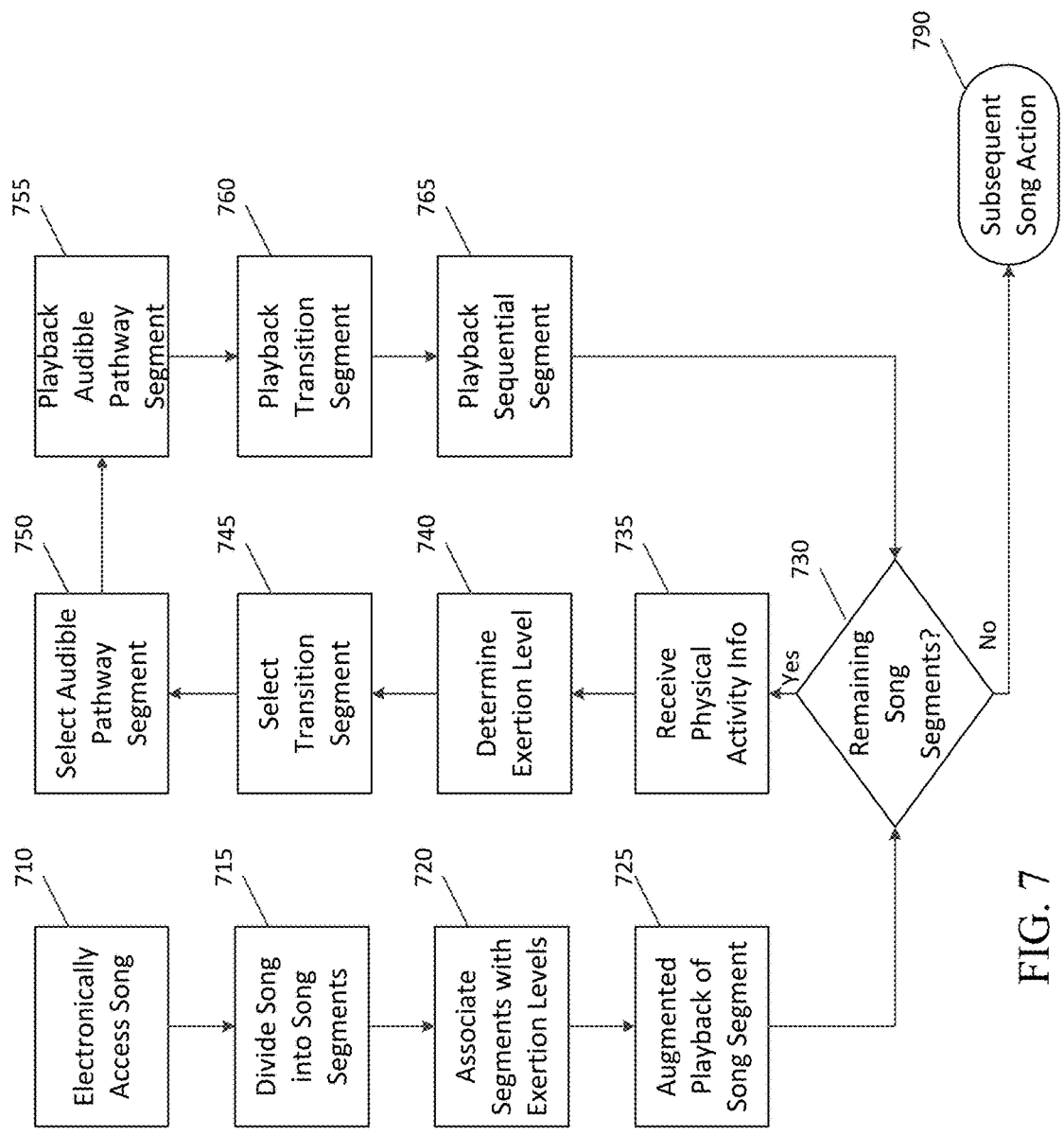
FIG. 7 shows a flowchart of a method for augmented playback of adaptive music during a physical activity.

FIG. 7 illustrates an embodiment of a process for adjusting the audible playback of a song according to detected changes in a physical activity level of a user. In some embodiments, some of the following steps may be accomplished by various components, systems or devices associated with an adaptive music playback system. It will be understood that in other embodiments one or more of the following steps may be optional.

At 710, an existing song is electronically accessed for audible playback to the user, e.g., upon receiving a user input selecting the existing song. The song may be composed of a plurality of audio layers that are individually and selectively overlaid on an entire duration of the existing song. The song may be divided into a plurality of sequential segments including at least a first and a last segment for a duration of the song at 715. The first segment may correspond to a beginning of the song and the last segment may correspond to an end of the song. Further, the plurality of sequential segments may include any number of middle segments in addition to the first and last segments. For example, the existing song may be segmented into a plurality of segments. Segmenting the existing song may include receiving audible characteristic information of the song and dividing the song into the plurality of segments based on the audible characteristic information. At 720, each of the plurality of sequential segments may be associated with an exertion level, i.e., a physical activity level, based upon audible characteristics of the segments as described herein.

At 725, augmented playback of the first segment of the existing song is initiating to the user. At 735, upon determining that there are remaining song segments of the song to be played at 730 (e.g., before initiating playback of the last segment of the song), physical activity derived from a sensor as described herein is received, corresponding to a real-time physical activity level of a user. The physical activity information may include a pace of the user and/or a heart rate of the user. Based on the physical activity information received, a real-time physical activity level of the user is obtained, e.g., an exertion level of the user with respect to at least one physical parameter is determined at 740.

Based on the determined exertion level, at 745 at least one of the plurality of sequential segments is selected as a candidate transition segment for transitioning playback of the song to. Based on the selected candidate transition segment, a plurality of audible pathways may be identified to transition the user to the selected candidate transition segment without playing all of any sequential segments between a current location of the existing song and the transition locations and each of the plurality of audible pathways is scored. At 750 a first pathway is selected from the plurality of audible pathways and at 755 the first pathway is audibly provided to the user to transition to playback of the candidate transition segment of the song. Subsequently, playback of the candidate transition segment is audibly provided to the user at 760 and a sequential segment is audibly provided to the user after the candidate transition segment at 765 and so on.

Throughout the playback of the song, the system will determine if there are a preset number of remaining song segments of the song to be play at 730. If there are remaining song segments, exertion levels associated with the physical activity information new transition segments of the may continue indefinitely or for an extended amount of time. Alternatively, if determined that there are not remaining song segments to be played at 730, a subsequent song action may occur at 790, e.g., ending the audible playback, repeating the song, selecting another song, and the like.

Figure 8:
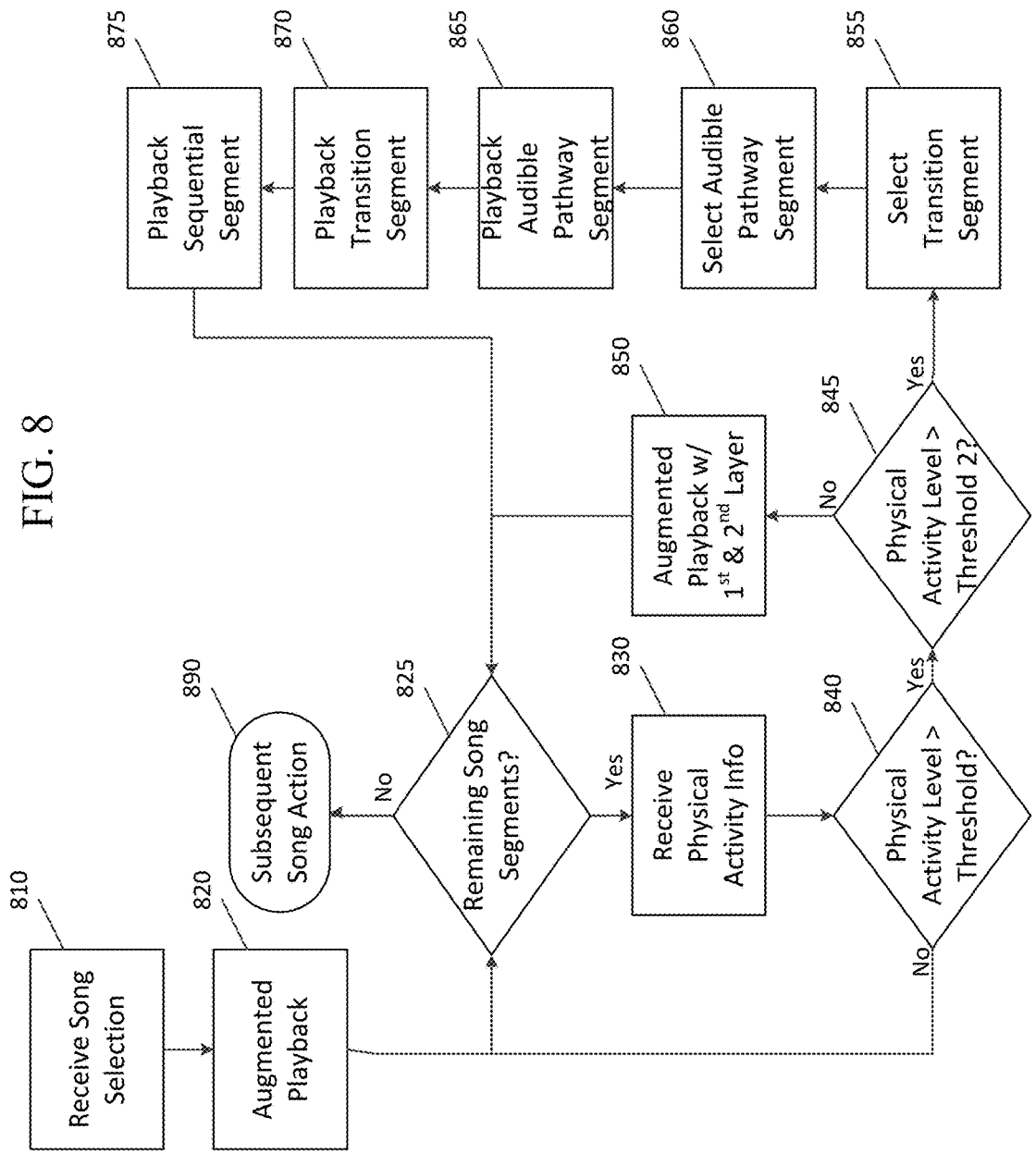
FIG. 8 shows a flowchart of a method for augmented playback of adaptive music during a physical activity.

IV. Example Adaptive Music Playback Systems with Audible Layers and Song Segments FIG. 8 illustrates an embodiment of a process for adjusting the audible playback of a song according to detected changes in a physical activity level of a user using audible layers (e.g., obtained with various stem files) and with song segments. In some embodiments, some of the following steps may be accomplished by various components, systems or devices associated with an adaptive music playback system. It will be understood that in other embodiments one or more of the following steps may be optional.

At 810, an existing song is electronically accessed for audible playback to the user, e.g., upon receiving a user input selecting the existing song. The song may be composed of a plurality of audio layers that are individually and selectively overlaid on an entire duration of the existing song. The duration may include a plurality of sequential segments including at least a first and a last segment. The first segment may correspond to a beginning of the song and the last segment may correspond to an end of the song. Further, the plurality of sequential segments may include any number of middle segments in addition to the first and last segments. For example, the existing song may be segmented into a plurality of segments. Segmenting the existing song may include receiving audible characteristic information of the song and dividing the song into the plurality of segments based on the audible characteristic information.

The plurality of audio layers may include first, second, and third layers. The plurality of audio layer may correspond to various musical instruments, for example, from a plurality of stem files associated with the song. In some examples, the first layer includes audio information for a first musical instrument, the second layer includes audio information for a second musical instrument that is not within the first layer, and the third layer includes audio information for a third musical instrument that is not within the first or second layers. In some examples, the first layer includes audio information for a first musical instrument, the second layer includes audio information for first and second musical instruments, and the third layer includes audio information for first, second and third musical instruments. The layers may correspond to various pluralities of musical instruments. In some examples, the first layer may comprise audio information for a first plurality of musical instruments and the second layer may comprise audio information for a second plurality of musical instruments. In some instances, musical instruments included in the first plurality of musical instruments may be excluded from the second plurality of musical instruments. In some examples, the third layer may include audio information configured to augment the audible perception of at least one of the first layer and the second layer when provided to the user. As referred to herein, musical instruments may include any number of various known instruments, voices and/or other sounds that can be stored as individual sound files. In some examples, one or more layers, e.g., higher layers, may include additional audio effects that are not included in the existing song. The layers may correspond to various stem files of the existing song. In some examples, the first layer may be composed of a first stem file and the second layer may be composed of a second stem file. Further the song may be composed of less than three layers or more than three layers without departing from the scope of these disclosures.

Each of the plurality of sequential segments may be associated with an exertion level, i.e., a physical activity level, based upon audible characteristics of the segments as described herein.

At 820, augmented playback of the first segment of the existing song is initiating to the user by audibly providing at least one layer of the song without at least one layer of the plurality of layers, e.g., the first layer of the song, but not the second layer of the song. In some examples, the plurality of layers of the existing song may be stored on a single non-transitory computer-readable medium prior to the user selecting the playback of the existing song, and the augmented playback of the existing song is from the single non-transitory computer-readable medium.

At 830, upon determining that there are remaining song segments of the song to be played at 825 (e.g., before initiating playback of the last segment of the song), physical activity derived from a sensor as described herein is received at a first instance, corresponding to a real-time physical activity level of a user. The physical activity information may include a pace of the user and/or a heart rate of the user. Based on the physical activity information received at the first instance, a real-time physical activity level of the user is obtained, e.g., an exertion level of the user with respect to at least one physical parameter is determined. The real-time physical activity level of the user may be compared to a first activity threshold to determine if the real-time activity level is above the first activity threshold at 840. In response to determining the physical activity level is above the first activity threshold, augmented playback of the existing song is continued by audibly providing the first layer and the second layer at 850. If the physical activity is determined to not be above the first activity threshold, playback with only the first layer may continue at 820. The second layer of the existing song may be received via a wireless transceiver.

After determining that the real-time physical activity level of the user is above the first activity level threshold, the real-time physical activity level may next be compared to a second activity level threshold to determine if the real-time activity is above a second activity level threshold 845. In response determining that the physical activity level is above the second activity threshold, at 855 at least one of a plurality of sequential segments is selected as a candidate transition segment for transitioning playback of the song to. Based on the selected candidate transition segment, at a plurality of audible pathways may be identified to transition the user to the selected candidate transition segment without playing all of any sequential segments between a current location of the existing song and the transition locations and each of the plurality of audible pathways is scored. At 860 a first pathway is selected from the plurality of audible pathways and at 865 the first pathway is audibly provided to the user to transition to playback of the candidate transition segment of the song. Subsequently, playback of the candidate transition segment is audibly provided to the user at 870 and a sequential segment is audibly provided to the user after the candidate transition segment at 875 and so on.

Throughout the playback of the first song, the system will determine if there are a preset number of remaining song segments of the song to be play at 825. If there are remaining song segments, the physical activity information may be compared to the various activity thresholds and the playback of the song with a number of layers may be modified accordingly. Alternatively, if determined that there are not remaining song segments to be played at 825, a subsequent song action may occur at 890, e.g., ending the audible playback, repeating the song, selecting another song, and the like.

A user selection may be received at any point during the physical activity identifying one or more parameters corresponding to the exertion level. Upon receiving a user selection setting or modifying parameters corresponding to exertion level, playback of the song may be modified, by modifying at least one of a number of layers and determining a pathway to a candidate transition segment.

A visualization of sensed physical activity and an energy level of the playback of the first music during the physical activity may be provided on a display during the physical activity. The display may be provided as part of various workout equipment, e.g., a screen of a treadmill, elliptical machine, stationary bike, and the like, or as part of a user device, such as a smartphone, tablet, laptop computer, or other digital device. In some example, the display may include a home screen prior to a user initiating an athletic activity. Upon starting the athletic activity, a visualizer may be provided on the display showing a relative exertion level of the user, as sensed by the one or more sensor and a level of music played during augmented playback.

V. Song Analysis for Example Adaptive Music Playback Systems

Figure 9:
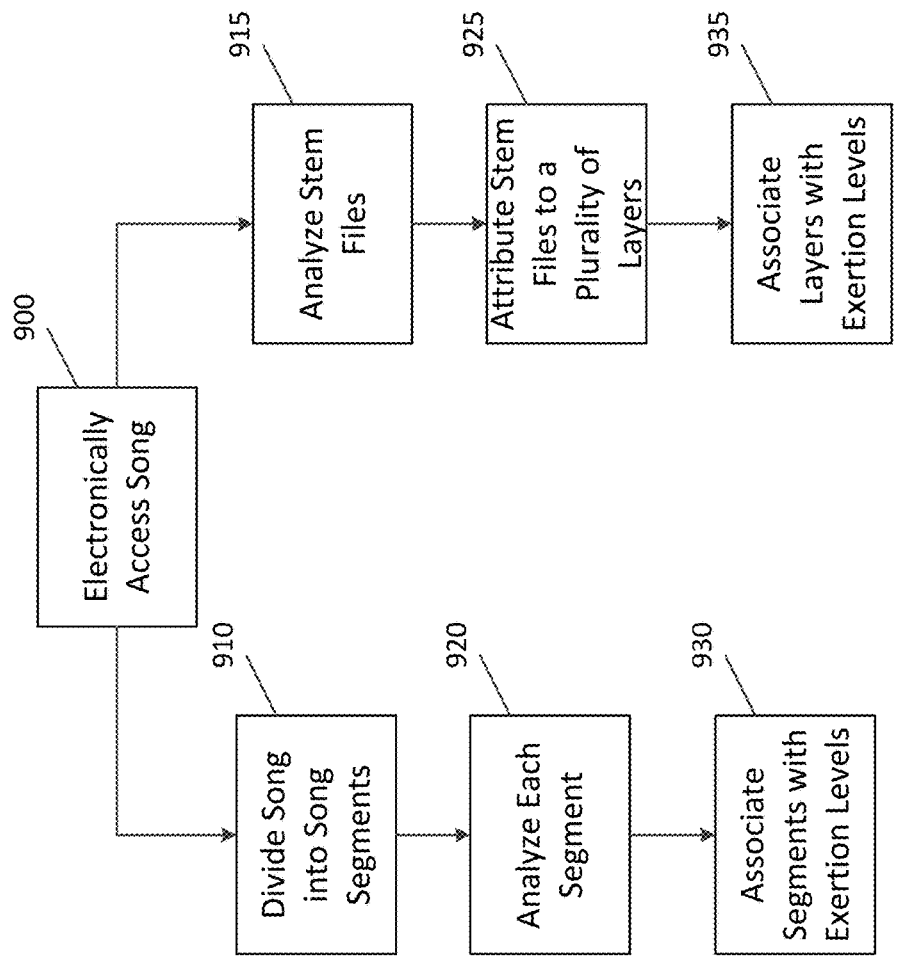
FIG. 9 shows a flowchart of a method of song analysis for augmented playback of adaptive music.

Algorithms for assessing sonic similarity between song segments may be used to assess each song segment. Algorithm for assessing an exertion level associated with each song segment may also be used. FIG. 9 illustrates a process for analyzing a song and using such algorithms to determine song layers and song segments as appropriate. At 910, an existing song is electronically accessed for analysis of adaptive playback features. The song may be locally saved to an electronic library or may be streamed from a music streaming service that stream song stem files.

Music analysis may be applied to a song in two aspects—temporal aspects and stem file layering aspects. In particular, music analysis may be used to provide additional structure and harmonic quality of the musical data beside simply the beat, including timbre (which assesses 12 aspect per beat to analyze the way a segment sounds), beats per bar, and loudness/pitch of bar beat (harmonic sound per beat.) Using a low level music analyzer, a beat level per bar may be obtained, which has experimentally been found to be a useful quantifier for an energy score during a physical activity. Beats per minute is a known metric for quantifying energy levels or exertion levels associated with a song.

Regarding the stem file layering aspects, the song may include a plurality of stem files; each included an audio component or components of the song, such as musical instruments or vocals. The stem files of the song may be analyzed at 915. A plurality of layers, e.g., five layers, may be assigned to a particular song, and each layer may correspond to one or more stem files. At 925, the stem files are attributed to the plurality of layers, and at 935 defined exertion level ranges are applied to each of the plurality of layers. In some examples, the layers include the same stem files throughout a duration of the song. In other examples, the layers modify the number of included stem files in each layer to maintain an associated energy level or exertion level per layer. The associated energy level or exertion level may correspond to a quantity measured by the sensor. For example, if the sensor is an accelerometer, the energy level or exertion level may be defined as ranges of pace or speed. If the sensor is a heart rate monitors, the energy level or exertion level may be defined in ranges of a measured heart rate for a particular user.

Regarding the temporal aspects, the song may be divided into a plurality of sequential segments (e.g., the smallest unit of audio that a human perceives as a distinct sound) including at least a first and a last segment for a duration of the song at 910 and each segment is analyzed at 920. Next, segments of the song may be identified that sound similar to other segments and may be labeled as such. This identification of similar sound segments allows for the ability for augmented playback of the song, with smooth transitioning to non-sequential segments of the song, without the user being able to audibly perceive jumping between non-sequential segments. For example, segments may be categorized according to various energy levels or exertion levels at 930. If augmented playback later occurs during a higher level energy level, the song may play only segments associated with the higher energy level and with transition segments, as discussed herein, to smoothly transition between non-sequential segments. Additionally audio effect may be applied as part of a transition segment to smoothly transition between non-sequential segments.

For example, a sonic or musical difference between two segments may be quantified using one or more variables, such as in an algorithm. Those skilled in the art will appreciate that a multitude of variables may be used depending on a plurality of factors. Examples of example variables that may be used, either alone or in combination with at one or more other variables (including other non-listed variables), includes:

p—"pitch"—A variable along the chromatic scale. In one embodiment, a set of values representing the harmonic measure of the twelve pitches of the chromatic scale (C, C#, D, etc.) may be implemented.

t—"timbre"—A set of values representing different characteristics of timbre of the segment. In certain embodiments, the value set for timbre may be the same for pitch. For example, if the variable set for pitch is 12, then the value set for timbre may be set to 12 as well. In yet other embodiments, the value set for timbre may be independent of the pitch. It may be 12 regardless of what the pitch value set is.

ls—"loudness"—The average volume of the segment.

lm—"loudness max"—The volume of the loudest point within the segment.

lmt—"loudness max time—The relative time from the start of the segment to its loudest point.

d—"duration"—The segment's time duration.

c—"confidence"—A percentage from 0%-100% indicating how confident that the characteristic values are accurate.

Those skilled in the art will appreciate that one or more variables above may be omitted without departing from the scope of this disclosure. Likewise, other variables and/or weights may be utilized. As noted from the above disclosure, the time shifting throughout the segment and adjustment of pitch by varying or augmenting playback of layers composed of various stem files, the tempo of a song may be modified without being able to audibly perceive a modification to the song, by using the methods and algorithms as discussed herein. Further, those skilled in the art will readily appreciate that each variable or collection of variables may be weighted. Weighting may be conducted with different mathematical principles for each variable. Weighting may be performed on only a portion or none of the variables. The scale of a weighting factor may be different for one or more variables with respect to the weighting for one of the variables used.

The song analysis may allow for musical matching wherein the augmented playback for the song may add in tracks of music (e.g., ad in stem files of the song and/or other audio effect) and may drops them out, as well as transitioning throughout temporal segments of the song smoothly to keep a high or lower level beat in a goal to inspire a user to keep to a pace via the musical matching. The song analysis may also be used to smooth transition, to smoothly transition to a cool down or reduced pace and/or to smoothly repeat a song maintaining the same energy level. By conducting the song analysis discussed herein, an automated system may be used to determine temporally where to go in a song and/or what layers of a song to add or drop to maintain or transition an energy level while continuously providing a smooth augmented playback of the song.

VI. Example Adaptive Music Playback Systems with Subsequent Song Determinations

FIG. 10 illustrates an embodiment of a process for subsequent song determinations according to determining that a preset number of segments remain in the song. At 1010, augmented playback of the first song is provided as discussed herein. In some examples, the plurality of layers of the existing song may be stored on a single non-transitory computer-readable medium prior to the user selecting the playback of the existing song, and the augmented playback of the existing song is from the single non-transitory computer-readable medium.

Augmented playback of the first song continues until determining that there are no remaining song segments, or that there is less than a preset number of remaining song segments, of the first song to be played at 1015. If the duration of the physical activity (set before starting the workout or upon receiving to user selection to stop the workout), is over at 1020, playback of the first song ends at 1090. If the activity is not ending, the system may next determine if the first song is to be repeated at 1025.

Based on determining to repeat the first song, at 1030 a plurality of audible pathways may be identified to transition augmented playback of the first song to a first segment and a first pathway or transition segment is selected from the plurality of audible pathways. At 1035 the first pathway is audibly provided to transition to playback of the first segment of the song. Augmented playback of the first segment of the first song is provided at 1040, and then the system continues with augmented playback of the first song at 1010 and so on.

Based on determining not to repeat the first song, at 1050 a plurality of audible pathways may be identified to transition augmented playback of to a first segment of a second song and a first pathway or transition segment is selected from the plurality of audible pathways. At 1055 the first pathway is audibly provided to transition to playback of the first segment of the second song. Augmented playback of the first segment of the second song is provided at 1060, and then the system continues with augmented playback of the second song.

The present application also extends to the subject-matter described in the following numbered paragraphs (referred to as "Para" or "Paras"):

1. A computer-implemented method comprising:
   receiving a user input from a user selecting an existing song for audible playback to the user, the song comprising a plurality of audio layers including at least a first layer, a second layer, and a third layer, wherein the first layer includes audio information for a first musical instrument and the second layer includes audio information for a second musical instrument;
   initiating augmented playback of the existing song to the user by audibly providing the first layer but not the second layer;
   receiving physical activity information derived from a sensor corresponding to a real-time physical activity level of a user; and
   determining that the real-time physical activity level of the user is above a first activity level threshold, and in response, continuing the augmented playback of the existing song by audibly providing the first layer and the second layer to the user.

2. The method of Para 1, wherein the third layer includes audio information configured to augment the audible perception of at least one of the first layer or the second layer when audibly provided to the user.

3. The method of Para 1, further comprising:
   after determining that the real-time physical activity level of the user is above the first activity level threshold, determining that the real-time physical activity level of the user is above a second activity level threshold, and in response, continuing the augmented playback of the existing song by audibly providing the first layer and the second layer to the user.

4. The method of Para 1, further comprising:
   receiving the second layer of the existing song via a wireless transceiver after the determining that the user is above the second activity level threshold.

5. The method of Para 1, further comprising:
   storing the plurality of layers of the existing song on a single non-transitory computer-readable medium prior to the user selecting the playback of the existing song, and the augmented playback of the existing song is from the single non-transitory computer-readable medium.

6. The method of Para 1, wherein the physical activity information comprises a pace of a user.

7. The method of Para 1, wherein the physical activity information comprises a heart rate of a user.

8. The method of Para 1, wherein the first layer is composed of a first stem file and the second layer is composed of a second stem file.

9. The method of Para 1, wherein the first layer comprises audio information for a first plurality of musical instruments and the second layer comprises audio information for a second plurality of musical instruments.

10. The method of Para 9, wherein the first plurality of musical instruments includes excludes the second musical instrument.

11. The method of Para 1, further comprising adjusting the playback of the song upon determining a change in the physical activity information, wherein adjusting the playback includes transitioning to a second combination of the one or more stem files of the first music content.

12. The method of Para 1, further comprising providing on a display a visualization of sensed physical activity and an energy level of the playback of the first music during the physical activity.

13. The method of Para 1, wherein adjusting the playback includes determining a second energy level corresponding to a pace of the physical activity information.

14. A computer-implemented method comprising:
   electronically accessing an existing song for audible playback to the user, the song comprising a plurality of audio layers that are individually and selectively overlaid an entire duration of the existing song,
   wherein the duration includes a plurality of sequential segments comprising at least a first segment and a last segment, and
   wherein the plurality of audio layers include at least a first layer, a second layer, and a third layer, wherein the first layer includes audio information for a first musical instrument and the second layer includes audio information for a second musical instrument that is not within the first layer;
   associating each of the plurality of segments with an exertion level based upon audible characteristics of the respective segments; initiating augmented playback of the first segment of the existing song to the user by audibly providing the at least one layer of the plurality of layers, however, without at least one layer within the plurality of layers;
   before initiating playback of the last segment, receiving, at a first instance, physical activity information derived from a sensor corresponding to a real-time physical activity level of the user;
   based on the physical activity information received at the first instance, determine an exertion level of the user with respect to at least one physical activity parameter;
   based on the determined exertion level, selecting at least one of the plurality of segments as a candidate transition segment for transitioning the user to;
   based on the selected candidate transition segment, identify a plurality of audible pathways to transition the user to the selected candidate transition segment without playing all of any sequential segments between a current location of the existing song and the transition locations;
   scoring each of the plurality of audible pathways; and
   selecting a first pathway from the plurality of audible pathways;
   audibly providing the user the first pathway of the existing song to arrive at the candidate transition segment.

audibly providing a sequential segment of the plurality of segments to the user following playback of the candidate transition segment.

15. The method of Para 14, further comprising:
segmenting the existing song into the plurality of segments, the segmenting comprising:
receiving audible characteristic information regarding the song, and
based upon the audible characteristic information, dividing the song into the plurality of segments.

16. A method comprising:
receiving a selection for a first music content;
initiating playback of the first music content at a first energy level, the first energy level corresponding to a first combination of one or more stem files of the first music content;
receiving a user selection identifying one or more parameters corresponding to a second energy level; and
adjusting the playback of the first music content from the first energy level to the second energy level, wherein adjusting the playback includes transitioning to a second combination of the one or more stem files of the first music content.

17. The method of Para 16, wherein transitioning to the second combination includes transitioning to a temporal location of the first music content, the temporal location corresponding to the second energy level.

18. A method of adjusting the playback of audio information, comprising:
playing a song, the song comprising a plurality of song segments that are sequential in time and the song further comprising a set of audio tracks that may be played simultaneously;
retrieving a set of composition rules, the composition rules including an algorithm for assessing sonic similarity between song segments and an algorithm for assessing an energy level of each song segments, wherein energy levels of song segments correspond to user activity levels;
receiving user activity information from at least one sensor configured to detect movements of a user;
determining a user activity level from the user activity information while a first song segment is being played;
finding a second song segment with a song state that matches the user activity level; and
using the composition rules to compose a musical transition from the first song segment to the second song segment.

19. A system comprising:
a sensor configured to detect physical activity information corresponding to real-time physical activity performed by a user; and
a user device configured to:
initiate augmented playback of a pre-existing first music content, the first music content comprising a plurality of layers and a plurality of music segments that are sequential in time, wherein playback of the first music content include one or more of the plurality of layers;
receive the physical activity information from the sensor;
determine an activity level of the user based on the physical activity information; and
modify the playback of the first music content based on the determined activity level, wherein modifying the playback includes modifying at least one of: a number of layers included in the playback of the first music content and a sequence of the plurality music segments.

20. The system of Para 19, wherein initiating the playback of the first music content includes initiating playback of only a first layer of the first music content, and wherein modifying the playback includes initiating playback of the first layer and one or more higher layers of the first music content.

21. The system of Para 19, wherein the user device is further configured to receive a user selection corresponding to the first music content selection.

22. The system of Para 19, wherein the user device is further configured to receive a user pace selection corresponding to a desired pace of the physical activity and wherein initiating playback of the first music content is modified based on the user pace selection.

23. The system of Para 19, wherein each layer corresponds to a different combination of instruments and/or vocals.

24. The system of Para 19, wherein a lowest layer of the plurality of layers includes one or more stem files of the first music content and corresponds to a lowest physical activity level, and wherein remaining layers of the plurality of layers include the one or more stem files of the first layer and additional stem files.

25. The system of Para 19, wherein a highest layer of the plurality of layers includes a repeated loop of a high energy music segment or a plurality of high energy music segments of the first music content and/or audio effects.

26. The system of Para 19, wherein modifying the playback of the first music content includes determining a music pathway portion of the first music content to smoothly transition through a song while maintaining a same level during playback.

27. The system of Para 26, wherein determining a music pathway portion includes sonic or timbre analysis of beats per bar and loudness/pitch of a bar beat to determine a musical transition portion.

28. The system of Para 27, wherein an energy score is applied to each beat level/bar and wherein the determining includes identifying sections of the first music content with similar energy scores and determining music pathway portions to transition to similar segments.

29. The system of Para 28, wherein determining a music pathway portion includes selecting a music pathway from a plurality of music pathways, and wherein a music pathway of shorter duration is preferred over a music pathway of longer duration.

30. The system of Para 26, wherein determining a music pathway portion is based on determining a sonic similarity between portions.

31. The system of Para 30, wherein sonic similarity is based on at least one of: pitch; timbre; average loudness; maximum loudness; maximum loudness time; segment duration; and parameter confidence.

32. The system of Para 19, wherein the plurality of layers of the first music content are determined based on a musical analysis of the stem files of the first music content.

33. The system of Para 32, wherein the musical analysis includes a determination of the most and least energetic loops of the first music content.

34. The system of Para 19, wherein the user device is further configured to, upon determining that playback of the first music content has exceeded a preset proximity to an end of the first music content, modify playback of the first music content to including playback of a music pathway portion to loop the first music content to a beginning portion of the first music content.

35. The system of Para 19, wherein the user device is further configured to, upon determining that playback of the first music content has exceeded a preset proximity to an end of the first music content, initiate playback of a second music content, the second music content having a similar level as the first music content.

36. The system of Para 19, wherein the plurality of layers of the first music content correspond to a plurality of activity levels of the physical activity information.

37. The system of Para 19, wherein the stem files of the first music content are streamed from a music streaming service.

38. The system of Para 19, wherein modifying the first music content includes adding one or more layers to the playback upon determining an increase in the physical activity, and removing one or more layers to the playback upon determining a decrease in the physical activity.

39. The system of Para 19, wherein an activity level is adjusted in response to a user activity selection.

40. The system of Para 19, wherein the user device is further configured to display a sensed activity level and an energy level of the music content selection during the physical activity.

41. The method of Para 19, wherein the physical activity information includes at least one of pace, distance, cadence, stride, acceleration, geolocation, and heartrate.

42. A computer-implemented method comprising:
electronically storing on a non-transitory computer-readable medium, a musical composition, the musical composition comprising a plurality of audio layers that are overlaid an entire duration of the musical composition, configured such that invoking normal playback of the musical composition causes the simultaneous playback of each of the plurality of audio layers in a synchronized manner,
wherein the plurality of audio layers include at least a first layer, a second layer, and a third layer, wherein the first layer includes audio information for a first musical instrument and the second layer includes audio information for a second musical instrument that is not within the first layer, and
wherein the duration of the musical composition is divided into a plurality of sequential segments comprising at least a first segment and a last segment;
associating each of the plurality of segments with an exertion level based upon audible characteristics of the respective segments;
initiating an augmented playback of the musical composition by initiating playback of the first segment of the musical composition to the user by audibly providing the at least one layer of the plurality of layers but less than all of the layers of the plurality of layers, wherein the augmented playback is configured to be conducted in a sequential manner through the sequential segments;
before initiating playback of the last segment of the sequential segment, receiving, at a first instance, physical activity information derived from a sensor corresponding to a real-time physical activity level of the user;
based on the physical activity information received at the first instance, determine an exertion level of the user with respect to at least one physical activity parameter;
based on the determined exertion level, selecting at least one of the plurality of segments other than the last segment as a candidate transition segment for transitioning the user to;
based on the selected candidate transition segment, identify a plurality of audible pathways to transition the user through to arrive at the selected candidate transition segment without playing all of any sequential segments between a current location of the musical composition and the selected candidate transition segment;
scoring each of the plurality of audible pathways;
selecting a first pathway from the plurality of audible pathways;
audibly providing the user the first pathway to arrive at the selected candidate transition segment; and
audibly providing a sequential segment of the plurality of segments to the user following playback of the candidate transition segment.

43. The method of claim 42, the claim further comprising:
prior to initiating the augmented playback of the musical composition, segmenting the existing song into the plurality of segments, the segmenting comprising:
receiving audible characteristic information regarding the song, and based upon the audible characteristic information, dividing the song into the plurality of segments.

What is claimed is:

1. A computer-implemented method comprising:
receiving a user input selecting an existing song for audible playback, the existing song comprising a plurality of audio layers comprising a first layer and a second layer, wherein the first layer includes audio information for a first musical instrument and the second layer includes audio information for a second musical instrument;
initiating augmented playback of the existing song by audibly providing the first layer but not the second layer;
receiving physical activity information derived from a sensor corresponding to a real-time physical activity level of a user;
in response to determining that the real-time physical activity level of the user is above a first activity level threshold, adjusting the augmented playback of the existing song by audibly providing the first layer and the second layer;
in response to reaching a predetermined segment in the adjusted augmented playback of the existing song and based on the determined real-time physical activity level, determining a transition segment of the existing song to transition to from a current segment of the existing song;
determining a plurality of pathways to reach the transition segment without playing all segments between a current segment and the transition segment, wherein each pathway of the plurality of pathways comprises one or more segments of the existing song and a pathway score;
selecting a first pathway of the plurality of pathways to arrive at the transition segment, wherein the first pathway is selected based on the respective pathway score; and
audibly providing the first pathway to arrive at the transition segment.

2. The method of claim 1, wherein the plurality of audio layers further comprises a third layer,
wherein the first layer is composed of a first stem file and the second layer is composed of a second stem file, and
wherein the third layer includes audio information configured to augment an audible perception of at least one of the first layer or the second layer, when audibly provided to the user.

3. The method of claim 2, further comprising:
upon determining that the real-time physical activity level of the user is above the first activity level threshold, determining that the real-time physical activity level of the user is above a second activity level threshold, and in response, further adjusting the adjusted augmented playback of the existing song by audibly providing the first layer, the second layer, and the third layer to the user.

4. The method of claim 1, wherein the first layer comprises audio information for a first plurality of musical instruments and the second layer comprises audio information for a second plurality of musical instruments.

5. The method of claim 4, wherein the first plurality of musical instruments excludes the second musical instrument.

6. The method of claim 1, further comprising upon determining a change in the physical activity information, adjusting the augmented playback of the existing song or the adjusted augmented playback of the existing song by transitioning to a second combination of one or more stem files of the existing song.

7. The method of claim 1, further comprising providing, on a display, a visualization of sensed physical activity and an energy level of the augmented playback or the adjusted augmented playback of the existing song during the physical activity.

8. The method of claim 1, wherein adjusting the augmented playback includes determining a second energy level corresponding to a pace of the physical activity information.

9. The method of claim 1, wherein the physical activity information comprises at least one of: a pace of the user and a heart rate of the user.

10. A system comprising:
a sensor configured to detect physical activity information corresponding to real-time physical activity performed by a user; and a user device configured to:
initiate augmented playback of a pre-existing first music content, the first music content comprising a plurality of layers and a plurality of music segments that are sequential in time, wherein augmented playback of the first music content includes one or more of the plurality of layers;
receive the physical activity information from the sensor; determine an activity level of the user based on the physical activity information; and
modify the augmented playback of the first music content based on the determined activity level,
wherein, when the determined activity level corresponds to a first activity level, modifying the augmented playback comprises modifying a number of layers included in the augmented playback of the first music content, and
wherein, when the determined activity level corresponds to a second activity level, modifying the augmented playback comprises modifying a sequence of the plurality of music segments included in the augmented playback of the first music content, wherein modifying the sequence of the plurality of music segments comprises:
determining, based on the determined activity level, a transition music segment of the first music content to transition to from a current music segment;
identifying a plurality of music pathways to transition the augmented playback of the first music content from the current music segment to the transition music segment, wherein each music pathway comprises one or more music segments of the first music content, and
selecting a first music pathway of the plurality of music pathways to arrive at the transition music segment, wherein the first music pathway is selected based on a corresponding pathway score.

11. The system of claim 10, wherein initiating the augmented playback of the first music content comprises initiating augmented playback of only a first layer of the first music content, and
wherein modifying the augmented playback, based on determining the first activity level, further comprises modifying the augmented playback of the first music content by audibly providing the first layer and one or more higher layers of the first music content.

12. The system of claim 10, wherein the user device is further configured to:
initiate the augmented playback of the pre-existing first music content in response to receiving a user selection corresponding to a first music content selection;
evaluate each music pathway of the plurality of pathways, based on a duration of the music pathway, to determine the pathway score for the music pathway; and
select, as the first music pathway, a music pathway having a pathway score indicating a shortest duration.

13. The system of claim 10, wherein the user device is further configured to receive a user pace selection corresponding to a desired pace of the physical activity, and wherein modifying the augmented playback of the first music content is further based on the user pace selection.

14. The system of claim 10, wherein each layer corresponds to a different combination of at least one of: instruments and vocals.

15. The system of claim 10, wherein a first layer of the plurality of layers includes one or more stem files of the first music content and corresponds to a lowest physical activity level, and wherein remaining layers of the plurality of layers include the one or more stem files of the first layer and additional stem files.

16. The system of claim 10, wherein a last layer of the plurality of layers includes at least one of: a repeated loop of a high energy music segment, a plurality of high energy music segments of the first music content, and audio effects.

17. The system of claim 10, wherein each music pathway of the plurality of music pathways comprises one or more music segments of the first music content having a sonic similarity, and
wherein modifying the augmented playback of the first music content based on determining the second activity level further comprises modifying the augmented playback of the first music content by:
audibly providing, in sequential order, the one or more music segments of the first music pathway, and
audibly providing the transition segment.

18. The system of claim 17, wherein the user device is further configured to:
perform sonic analysis of beats per bar and loudness of a bar beat of each music segment of the plurality of music segments of the first music content to determine the music transition segment.

19. The computer-implemented method of claim 1, wherein the one or more segments have similar sonic characteristics, and
wherein audibly providing the first pathway comprises:
audibly providing each of the one or more segments in the first pathway in sequential order, and
audibly providing the transition segment.

20. The computer-implemented method of claim 1, further comprising:

evaluating each pathway, based on a duration of the pathway, to determine the pathway score for the pathway; and selecting, as the first pathway, a pathway, of the plurality of pathways, having a shortest duration.

* * * * *